US007632409B2

(12) United States Patent  
Little et al.

(10) Patent No.: US 7,632,409 B2  
(45) Date of Patent: Dec. 15, 2009

(54) CATION-EXCHANGE DISPLACEMENT CHROMATOGRAPHY PROCESS AND CATIONIC ORGANIC COMPOUNDS FOR USE AS DISPLACER COMPOUNDS IN CATION-EXCHANGE DISPLACEMENT CHROMATOGRAPHY PROCESS

(75) Inventors: Charles Little, Austin, TX (US); Victor van de Pas, Zalthommel (NL); Barry Haymore, Austin, TX (US)

(73) Assignee: SACHEM, Inc., Austin, TX (US)

( * ) Notice: Subject to any disclaimer, the term of this patent is extended or adjusted under 35 U.S.C. 154(b) by 526 days.

(21) Appl. No.: 11/551,765

(22) Filed: Oct. 23, 2006

(65) Prior Publication Data

US 2007/0102363 A1 May 10, 2007

Related U.S. Application Data

(63) Continuation-in-part of application No. 11/267,823, filed on Nov. 4, 2005, now abandoned.

(51) Int. Cl.  
*B01D 15/08* (2006.01)

(52) U.S. Cl. .................. 210/635; 210/656; 210/659; 210/198.2; 530/413; 530/416; 530/417

(58) Field of Classification Search ........ 210/635, 210/656, 659, 198.2; 530/413, 416, 417  
See application file for complete search history.

(56) References Cited

U.S. PATENT DOCUMENTS

| 4,554,021 | A | | 11/1985 | Harvey et al. ............ 106/213 |
|---|---|---|---|---|
| 5,252,216 | A | * | 10/1993 | Folena-Wasserman et al. ............ 210/635 |
| 5,478,924 | A | * | 12/1995 | Cramer et al. ............ 530/416 |
| 5,545,328 | A | * | 8/1996 | Pliura et al. ............ 210/635 |
| 5,606,033 | A | | 2/1997 | Cramer et al. ............ 530/416 |
| 5,616,800 | A | | 4/1997 | Roerden et al. ............ 564/292 |
| 6,177,577 | B1 | | 1/2001 | Roerden et al. ............ 549/551 |
| 6,239,262 | B1 | * | 5/2001 | Cramer et al. ............ 530/417 |
| 6,376,583 | B1 | | 4/2002 | Winkler et al. ............ 524/47 |
| 6,929,747 | B2 | | 8/2005 | Cramer et al. ............ 210/635 |
| 2005/0194113 | A1 | | 9/2005 | Lang et al. ............ 162/175 |
| 2007/0125712 | A1 | * | 6/2007 | Little et al. ............ 210/656 |

FOREIGN PATENT DOCUMENTS

EP 1 064 312 B1 11/2002

OTHER PUBLICATIONS

International Search Report and Written Opinion of the International Searching Authority, Application No. PCT/US2006/034450, mailed Dec. 29, 2006.

Keana et al.; Di, Tri-, Tetra-, and Pentacationic Alkylammonium Salts. Ligands Designed to Prevent the Nonspecific Electrostatic Precipitation of Polyanionic, Functionalized Cyclopentadienyltitanium-Substituted Heteropolytungstate Electron Microscopy Labels with Cationic Biomolecules; *J. Org. Chem.*, 1987, 51, pp. 2571-2576.

Tugcu et al.; "Stationary phase effects on the dynamic affinity of low-molecular-mass displacers"; *Journal of Chromatography A*, 954, 2002, pp. 127-135.

Shukla et al.; "Structural characteristics of low-molecular-mass displacers for cation-exchange chromatography"; *Journal of Chromatography A*, 814, 1998, pp. 83-95.

* cited by examiner

*Primary Examiner*—Ernest G Therkorn  
(74) *Attorney, Agent, or Firm*—Renner, Otto, Boisselle & Sklar, LLP

(57) ABSTRACT

A displacement chromatography process and displacer compounds used in the process and having the general formula (I):

-continued wherein:

each group $R_1$, $R_2$, $R_3$, $R'_1$, $R'_2$, and $R'_3$, independently may be selected from alkyl, aryl, and aralkyl, and in which a ring containing one or more quaternary nitrogen may be formed by any one or more of $R_1$ and $R_2$, $R_1$ and $R'_1$, $R_1$ and $R_4$, $R_4$ and $R'_4$, or $R_4$ and $R_5$;

each $R_4$, $R'_4$, $R_5$ and $R'_5$ independently may be selected from alkyl, aryl, aralkyl and $-(CH_2)_a-(CHY)_b-(CH_2)_c-N^+R_1R_2R_3$ An$^-$, wherein $R_1$, $R_2$ and $R_3$ are as defined above;

each Y independently may be selected from $-$H, $-$OH, $-$OR$_6$, halo, alkyl, aryl and aralkyl, wherein $-$R$_6$ may be alkyl or $-(CH_2)_a-(CHOH)_b-(CH_2)_c-N^+R_1R_2R_3$ An$^-$, wherein $R_1$, $R_2$ and $R_3$ are as defined above;

each q and z independently may be any whole number from 0 to about 6, with the proviso that q+z is equal to or less than about 6;

each a, b, and c independently may be any whole number from 0 to 2, with the proviso that the sum a+b+c in any fragment is at least 1; and each An$^-$ independently may be one or more organic or inorganic, monovalent or polyvalent anion as needed to obtain a neutral compound.

32 Claims, 4 Drawing Sheets

CATION-EXCHANGE DISPLACEMENT CHROMATOGRAPHY PROCESS AND CATIONIC ORGANIC COMPOUNDS FOR USE AS DISPLACER COMPOUNDS IN CATION-EXCHANGE DISPLACEMENT CHROMATOGRAPHY PROCESS

CROSS-REFERENCE TO RELATED APPLICATION

The present application is a continuation-in-part of and claims priority under 35 U.S.C. §120 to commonly assigned U.S. application Ser. No. 11/267,823, filed 4 Nov. 2005, now abandoned, the entirety of which is hereby incorporated by reference.

TECHNICAL FIELD

The present invention pertains to compositions comprising multiple quaternary ammonium salts (multiple quats), and processes of using said compositions as displacers in chromatographic purifications.

BACKGROUND

The displacement mode of chromatography was first recognized in 1906 by Tswett, who noted that sample displacement occurred under conditions of overloaded elution chromatography. In 1943, Tiselius proposed that the broad subject of chromatography could be organized around three distinct "modes:" frontal mode, elution mode, and displacement mode. Since then, most developments and applications, particularly those in analytical chromatography, have taken place in the area of elution chromatography. Indeed, the term "chromatography" without further qualification today usually refers to chromatography in the elution mode.

Elution mode and displacement mode are readily distinguished both in theory and in practice. In elution chromatography, a solution of the sample to be purified is applied to a stationary phase, commonly in a column. The mobile phase is chosen such that the sample is neither irreversibly adsorbed nor totally non-adsorbed, but rather binds reversibly. As the mobile phase is flowed over the stationary phase, an equilibrium is established between the mobile phase and the stationary phase whereby, depending upon the affinity for the stationary phase, the sample passes along the column at a speed which reflects its affinity relative to other components that may be present in the original sample. Of particular note in standard elution chromatography is the fact that the eluting solvent front, or zero column volume in isocratic elution, always precedes the sample off the column.

A modification and extension of isocratic elution chromatography is found in step gradient chromatography wherein a series of eluents of varying composition are passed over the stationary phase. In ion-exchange chromatography, for example, step changes in the mobile phase salt concentration and/or pH are employed to elute or desorb analytes undergoing separation.

Displacement chromatography employs a displacer compound to remove components of a mixture from the column. The displacer compound generally has a much higher affinity for the stationary phase than do any of the components in the mixture to be separated. This is in contrast to elution chromatography, where the eluent has a lower affinity for the stationary phase than do the components to be separated. A key operational feature that distinguishes displacement chromatography from elution or desorption chromatography is the use of a displacer compound. In displacement chromatography, the column is first equilibrated with a carrier solvent under conditions in which the components to be separated all have a relatively high affinity for the stationary phase. A volume of feed mixture, which can be large and quite dilute, is loaded onto the column and individual components in the feed mixture will adsorb to the stationary phase. That is, the components of the feed mixture are distributed and adsorbed onto the stationary phase, and remain there. If all the components are to be resolved by displacement, the carrier solvent emerges from the column containing no sample. The components of the feed mixture now reside on the stationary phase, and the position of each component on the column is correlated with its relative affinity for the stationary phase under the initial conditions. In principle, a molecule of any component will displace a molecule of any different component having a lower affinity at a given site on the stationary phase. As a result, individual components will ultimately be arranged on the column in sequence from highest to lowest affinity.

It is sometimes advantageous to allow some components of the feed mixture, e.g., components not having a significant affinity for the stationary phase, to pass through the column with the carrier solvent; in this case only the retained feed components will be resolved by displacement chromatography.

Once the sample is loaded on the column, a solution containing a displacer compound in a suitable solvent is introduced into the column to pass through the stationary phase. The displacer compound is selected such that it has a higher affinity for the stationary phase than do any of the components of the feed mixture. Assuming that the displacer and mobile phase are appropriately chosen, the individual components exit the column as adjacent zones of highly concentrated, relatively pure material in the order of increasing affinity of absorption. Following the zones of the purified individual components, the displacer emerges from the column. A displacement chromatogram is readily distinguished from an elution chromatogram by virtue of the fact that the displacer compound follows the sample and that the feed components exit the column as adjacent zones of highly concentrated, relatively pure material.

Displacement chromatography has some particularly advantageous characteristics for process scale chromatography. First, displacement chromatography can achieve product separation and concentration in a single step. By comparison, isocratic elution chromatography results in significant product dilution during separation. Second, since the displacement process operates in the nonlinear region of the equilibrium isotherm, high column loadings are possible. This allows much better column utilization than elution chromatography. Third, column development and component separation requires less solvent than a comparable elution process. Fourth, displacement chromatography can concentrate and purify components from mixtures having low separation factors, while relatively large separation factors are required for satisfactory resolution in typical elution chromatography.

With all of these advantages, one might presume that displacement chromatography would be widely utilized. However, problems have persisted in displacement chromatography. One such problem is the need to regenerate the column, since it would not be economical to discard the stationary phase after each use. Another such problem is obtaining suitable displacer compounds that are relatively simple compounds, easily synthesized and/or commercially available at a reasonable (economical) cost. These two problems have presented significant drawbacks to displacement chromatography vis-a-vis elution chromatography.

With respect to regeneration, since the displacement process uses a displacer compound having a very high affinity for the stationary phase, the time needed to regenerate and re-equilibrate the column can be long compared to elution chromatography. Furthermore, relatively large amounts of solvent are often required during regeneration. These problems have effectively reduced the advantages of displacement chromatography over elution chromatography.

The second problem, that of obtaining useful displacer compounds that can be synthesized relatively easily and/or that are commercially available at a reasonable (economical) cost, is due to the need for a displacer compound that has both a high affinity for the stationary phase but that can also be relatively easily removed from the column during regeneration. Such compounds that have been offered by the prior art do not meet one or both of these two important criteria. Various compounds have been offered as low molecular weight displacers, but these have been quite difficult to synthesize and purify and have not been commercially available at reasonable cost, or simply not commercially available.

In order for displacement chromatography to become a mainstream chromatographic technique, there remains a significant unmet need for effective displacers whose synthesis and purification are straightforward and that are amenable to large-scale production, and/or that are commercially available, and which allow for efficient regeneration of the stationary phase so that the stationary phase can be subsequently reused in displacement chromatography processes.

SUMMARY

It has now been found that a class of positively charged compounds of low molecular weight can function very efficiently as displacer compounds in a displacement chromatography process. Thus, the present invention relates to both a displacement chromatography process and a group of displacer compounds. The displacer compounds in accordance with the present invention may be efficiently removed from the stationary phase after being used as the displacer compound in a displacement chromatography process, allowing for regeneration and re-use of the stationary phase in subsequent displacement chromatography processes. Furthermore, these displacer compounds can be made in good yield and in high purity, by relatively straightforward and inexpensive synthetic methods. Thus, the present invention addresses the aforementioned problems in displacement chromatography processes of the prior art.

The displacer compounds in accordance with an embodiment of the present invention belong to a class of compounds known as organic quaternary ammonium salts (quat salts). Quat salts are compositions comprising positively-charged nitrogen atoms. These compositions comprise aliphatic chains, yet nevertheless can be water soluble in many instances. When soluble in water, these compounds exhibit the useful property of having positive charges that are unaffected by changes in pH. That is, the charge on the nitrogen center is not the result of simple protonation of an amine, so the pH of aqueous solutions of these salts may be adjusted over a wide range without causing the loss of the positive charge on the nitrogen center. Common polyamines and related compounds are usually not useful as displacer compounds in cation-exchange displacement chromatography. This is because they are not fully protonated—and therefore do not develop sufficient positive charge—in pH ranges that are compatible with displacement chromatography resins. In contrast, the displacer compounds of the present invention can be used in any pH range at which the chromatography resin is stable.

In one embodiment, the present invention relates to a displacement chromatography process, comprising:

loading onto a suitable stationary phase a mixture comprising at least one component to be separated;

displacing said at least one component from the stationary phase by applying to the stationary phase a mixture comprising a displacer compound having general formula (I):

wherein:

each group $R_1$, $R_2$, $R_3$, $R'_1$, $R'_2$, and $R'_3$, independently may be selected from alkyl, aryl, and aralkyl, and in which a ring containing one or more quaternary nitrogen may be formed by any one or more of $R_1$ and $R_2$, $R_1$ and $R'_1$, $R_1$ and $R_4$, $R_4$ and $R'_4$, or $R_4$ and $R_5$;

each $R_4$, $R'_4$, $R_5$ and $R'_5$ independently may be selected from alkyl, aryl, aralkyl and $-(CH_2)_a-(CHY)_b-(CH_2)_c-N^+R_1R_2R_3$ $An^-$, wherein $R_1$, $R_2$ and $R_3$ are as defined above;

each Y independently may be selected from $-H$, $-OH$, $-OR_6$, halo, alkyl, aryl and aralkyl, wherein $-R_6$ may be alkyl or $-(CH_2)_a-(CHOH)_b-(CH_2)_c-N^+R_1R_2R_3$ $An^-$, wherein $R_1$, $R_2$ and $R_3$ are as defined above, and one or more Y may be a group detectable by one or more electromagnetic methods;

each q and z independently may be any whole number from 0 to about 6, with the proviso that q+z is equal to or less than about 6;

each a, b, and c independently may be any whole number from 0 to 2, with the proviso that the sum a+b+c in any fragment is at least 1; and each $An^-$ independently may be one or more organic or inorganic, monovalent or polyvalent anion as needed to obtain a neutral compound.

In one embodiment, the present invention relates to a composition defined by the general formula (I) above. In one embodiment, the present invention relates to a composition having the following structure and referred to as TBTQ-A:

In one embodiment, a composition in accordance with the general formula (I) is other than DBQ, DMTQ, DBTQ, BTA and DBD, each having a structure as defined hereinbelow.

In one embodiment, the present invention relates to a displacer composition useful in displacement chromatography. In one embodiment, the displacer composition includes, in a suitable aqueous solution, a compound of general formula (I) as shown above. In one embodiment, the present invention relates to a displacer composition useful in displacement chromatography having the above structure and identified as TBTQ-A. In one embodiment, the displacer composition is other than DBQ, DMTQ, DBTQ, BTA and DBD.

In one embodiment, the present invention provides a process for one or more of detection, collection or quantification of trace components in the sample subjected to displacement chromatography.

Thus, the present invention provides displacer compounds, compositions and processes for displacement chromatography which addresses the need for effective displacer compounds whose synthesis and purification are straightforward and amenable to large-scale production, which allow for efficient regeneration of the stationary phase so that the stationary phase may be reused efficiently. In addition, the present invention provides a process by which trace components of the sample or mixture may be detected, collected and/or quantified.

DETAILED DESCRIPTION

As used herein "halo" refers to a group comprising a halogen, such as chloro, bromo, fluoro, or iodo.

As used herein, "alkyl" and "alkylene" refer to a group of carbon and hydrogen atoms derived from an alkane molecule by removing one or two hydrogen atoms, as appropriate. "Alkyl" and "alkylene" may include saturated monovalent and divalent hydrocarbon radicals having straight, cyclic or branched moieties. The "alkyl" or "alkylene" groups may include an optional carbon-carbon double or triple bond where said alkyl group comprises at least two carbon atoms. It is understood that for cyclic moieties at least three carbon atoms are required in said alkyl group. In the present invention, alkyl and alkylene groups may include any number of carbon atoms. In one embodiment of the present invention, about 20 or less carbon atoms may be used. For example, in one embodiment, alkyl groups of 2, 3, 4, 5, 6, 7, 8, 9, 10, 11, 12, 13, 14, 15, 16, 17, 18, 19, or 20 carbons may be employed in the present invention. Of course, alkyl groups of longer length or branched may be employed in the present invention. Alkylene groups may be used, for example, in an embodiment in which a ring is to be formed from two groups that would otherwise be alkyl groups.

As used herein, "aryl" refers to an unsubstituted or substituted aromatic structure such as phenyl, naphthyl, fluorenyl, phenanthryl, etc. The aryl group, when substituted, may be substituted by a halo group, an alkyl group, another aryl group or an aralkyl group, as defined herein.

As used herein, "aralkyl" refers to a radical in which an aryl group is substituted for a hydrogen atom of an alkyl group. "Aryl" is as defined above. In the present invention, aralkyl groups may include any number of carbon atoms. In one embodiment of the present invention, the aralkyl group contains about 20 or less carbon atoms. For example, in one embodiment, aralkyl groups of 7, 8, 9, 10, 11, 12, 13, 14, 15, 16, 17, 18, 19, or 20 carbons may be employed in the present invention. Of course, aralkyl groups of more carbon atoms may be employed in the present invention.

As used herein, "An$^-$" represents one or more organic or inorganic, monovalent or polyvalent anions associated with the displacer compounds of the present invention. The number and total charge of the negatively-charged anions associated with the quaternary ammonium ions of the present invention will vary depending on the pH of the mixture and on the anion of the acid or acids used for neutralization. The anions, An$^-$, of the present invention may be any organic or inorganic, monovalent or polyvalent anion known to those of skill in the art, including monovalent, divalent and multivalent anions such as sulfonate, triflate, trifylamide, carboxylate, $F^-$, $Cl^-$, $Br^-$, $I^-$, $ClO_3^-$, $HSO_4^-$, $SO_4^{2-}$, $PO_4^{3-}$, $HPO_4^{2-}$, $H_2PO_4^-$, $PO_3^{2-}$, $HPO_3^-$, $BF_4^-$, $PF_6^-$ and the like. In general, the valence and number of An$^-$ can be suitably selected as needed to obtain a neutral compound.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 and the like, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Cationic Displacer Compounds

The cationic displacer compounds of the instant invention include those having the formula (I):

wherein each group $R_1$, $R_2$, $R_3$, $R'_1$, $R'_2$, and $R'_3$, may be independently selected from alkyl, aryl, and aralkyl, and in which a quaternary nitrogen-containing ring may be formed by any one or more of $R_1$ and $R_2$, $R_1$ and $R'_1$, $R_1$ and $R_4$, $R_4$ and $R'_4$ or $R_4$ and $R_5$;

each $R_4$ and $R_5$ is independently selected from alkyl, aryl, aralkyl and —$(CH_2)_a$—$(CHY)_b$—$(CH_2)_c$—$N^+R_1R_2R_3$ $An^-$, wherein $R_1$, $R_2$ and $R_3$ are as defined above;

each Y may be independently selected from —H, —OH, —$OR_6$, halo, alkyl, aryl and aralkyl, wherein —$R_6$ may be alkyl or —$(CH_2)_a$—$(CHOH)_b$—$(CH_2)_c$—$N^+R_1R_2R_3$ $An^-$, wherein $R_1$, $R_2$ and $R_3$ are as defined above, and one or more Y may be a group detectable by one or more electromagnetic methods;

q and z each may be any whole number from 0 to about 6, with the proviso that q+z is equal to or less than about 6;

a, b, and c each may be any whole number from 0 to 2, with the proviso that the sum a+b+c in any fragment is at least 1; and

$An^-$ may be one or more organic or inorganic, monovalent or polyvalent anion as needed to obtain a neutral compound.

A displacer compound of formula (I) may contain an additional substituent that makes it easily detected by UV/Vis spectroscopy, by fluorescence, or any other method known to those skilled in the art. Such a substituent might also influence the affinity of the compound for cation-exchange chromatography, making it either less strongly bound or more strongly bound. In some cases it would be advantageous to have no substituent that would interfere with the normal means of detecting the compounds being purified by displacement chromatography. An example of this latter case would be a displacer compound of formula I that does not absorb UV light at 280 nm, a wavelength at which certain biopolymers (proteins, oligopeptides, antibodies, etc.) characteristically absorb. Suitable derivatizing agents for enhancing detectability are known to and can be suitably selected by those of skill in the art.

In one embodiment, one or more Y in the displacer compound in accordance with the present invention may be a group detectable by one or more electromagnetic methods. Such electromagnetic methods include, for example, UV/visible spectrophotometry, fluorescence spectrophotometry, and radioactive detection methods. Suitable Y groups and appropriate methods for detecting such Y groups are known to those of skill in the art for use with such methods.

Suitable, exemplary cationic displacer compounds include, for example, the following specific examples, wherein, in each case, $An^-$ may be one or more organic or inorganic, monovalent or polyvalent anion, with the number and valence of each $An^-$ suitably selected to provide a neutral compound (that is, each molecule should have zero net charge, the positive and negative charges on the respective ions being balanced). The following specific compounds are provided as examples of the displacer compounds defined by the general formula (I) set forth above, including substituents as defined therein. The following examples are not intended to be limiting, but are instead intended to provide specific examples illustrating displacer compounds in accordance with various embodiments of the invention.

DBQ, having the structural formula:

DMTQ, having the structural formula:

DBTQ, having the structural formula:

TBTQ-A, having the structural formula:

BTA, having the structural formula:

DBD, having the structural formula:

wherein in each such structure (i.e., DBQ, DMTQ, DBTQ, TBTQ-A, BTA and DBD), An⁻ may be one or more organic or inorganic, monovalent anion, or An⁻ may be a polyvalent anion, in which case a suitable number of such moieties are present to obtain a neutral molecule. This definition and use of An⁻ applies throughout this disclosure.

An exemplary displacer compound including a quaternary nitrogen-containing ring, in which $R_4$ is bonded to $R'_4$ through an ethylene group, in which all of $R_1, R_2, R_3, R'_1, R'_2, R'_3, R_5$ and $R'_5$ are methyl, An⁻ is as defined above, and in which Y=—OH has the following structural formula:

In one embodiment, the displacer compound of the present invention is free of ether groups in the molecule. In one embodiment, the displacer compounds of the present invention are free of ether groups connecting adjacent quaternary nitrogen atoms. In one embodiment, the displacer compounds of the present invention comprise polyquaternary groups in which adjacent polyquaternary groups are not connected by ether-containing moieties. In one embodiment, the displacer compounds of the present invention are free of a dendritic polyether. In one embodiment, the displacer compounds of the present invention comprise quaternary nitrogen atoms which are not linked together by a group obtained from an ether or polyether.

In accordance with one embodiment of the present invention, the suitable stationary phase is a cation-exchange resin. Suitable cation-exchange resins are known in the art, and generally include resins such as methacrylate, silica, polystyrene or polystyrene-divinylbenzene, which have been derivatized with an anionic moiety, such as carboxymethyl, sulfopropyl, sulfonic acid, carbonic acid, etc., to which cations are attracted. Suitable cation-exchange materials can be selected by those of skill in the art based on the type of materials to be separated. In one embodiment, suitable cation-exchange resins for use with the present invention include, for example, Tosoh SP-5PW, Tosoh CM-650, SP-650 and SP-550, TOYOPEARL® Super-Q 650S, TOYOPEARL® CM 650S, and TSK Gel SP-5PW cation-exchange resins, available from Tosoh Corp., Tokyo, Japan and Montgomeryville, Pa. Additional suitable cation-exchange resins include, for example, UnoSphere S and MacroPrep S/MacroPrep High-S, available from Bio-Rad Laboratories (Hercules, Calif.); CHIROBIOTIC®, available from Advanced Separation Technology (Whippany, N.J.); SP-8HR and SP-15 HR, available from Waters Corporation (Milford, Mass.); Mini S, Source 15S, Mono S, SP SEPHAROSE® HP, and SP SEPHAROSE® FF, available from GE-Amersham Biosciences (Piscataway, N.J.); SHOWDEX® IEC SP-825 and SHOWDEX® IEC SP-2025, available from Showa Denko (New York, N.Y.); PL-SCX, available from Polymer Laboratories (Amherst, Mass.); Macrosphere300, available from Alltech Laboratories (Deerfield, Ill.); PolySulfoEthylA, available from PolyLC, Inc. (Columbia, Md.); and FRACTOGEL® EMD SE Hicap and FRACTOGEL® EMD SO3, available from EMD Chemicals Inc. (Gibbstown, N.J.). Other suitable cation-exchange resins may be used as well.

In accordance with one embodiment of the present invention, the displacement chromatography process can be used to separate and purify proteins and polypeptides. As used herein, a protein is broadly defined as a polyamino acid having a molecular weight greater than about 5 kDa (kilo Daltons), and a polypeptide is a polyamino acid having a molecular weight less than about 5 kDa. As will be understood by those of skill in the art, the difference between a protein and a polypeptide is more one of degree. In general, a protein exhibits tertiary structure, while a polypeptide generally does not.

In one embodiment, the present invention is particularly applicable to separation of components such as proteins and polypeptides from mixtures containing such components. In one embodiment, the one or more component in the mixture comprises one or more polypeptide, one or more protein or a mixture of any two or more such protein and/or polypeptide. That is, the process of the present invention is applicable for separation of mixtures of proteins, mixtures of polypeptides and mixtures of both a protein and a polypeptide In one embodiment, the one or more protein comprises a molecular weight of about 5 kD or higher. In one embodiment, the mixture comprises two or more proteins, two or more polypeptides or a mixture thereof.

In one embodiment, a protein and/or polypeptide from the mixture is displaced from the stationary phase in a fraction in which the protein and/or polypeptide is substantially enriched and/or in which the protein and/or polypeptide is substantially separated from other protein and/or polypeptide components. That is, in one embodiment, when a mixture containing the protein or polypeptide of interest is applied to the stationary phase, when the protein or polypeptide is displaced from the stationary phase and is collected in one or more fraction, the protein and/or polypeptide is obtained in the fraction in either or both of an enriched, i.e., more concentrated, form, or is obtained substantially separated from other, different proteins and/or polypeptide components in the original mixture. Thus, clearly the mixture may include two or more components to be separated. As discussed in the following, in some embodiments, the mixture subjected to displacement chromatography in accordance with the present invention may include a combination of many different materials from a variety of different sources, and the process of the present invention may be usefully applied to such complex mixtures to separate the various components thereof.

In another embodiment, the present invention is applicable to a mixture containing at least one component (such as protein, polypeptide or other, as defined below) and at least one impurity. In this embodiment, the process of the present invention may be used to purify the component from impurities. Such removal of impurities may be either (1) by immobilization or retention on the stationary phase after the sought or desired component has been displaced (e.g., where the stationary phase acts as a filter), or (2) by being washed out of or eluted from the stationary phase, where the impurity is removed by a means more similar to "traditional" elution chromatography. In this embodiment, when the impurity has been either immobilized on or removed from the column, the desired component can then be removed from the column by displacement chromatography as described herein.

The present invention is applicable to a wide variety of components, including not only the above-mentioned proteins, polypeptides, and impurities, but many other components. In one embodiment, the mixture may include one or more, natural or recombinant, antibody or a mixture of any two or more such antibodies. In one embodiment, the mixture may include one or more, natural or recombinant, enzyme or a mixture of any two or more such enzymes. In one embodiment, the mixture may include one or more, natural or recombinant, protein or polypeptide for diagnostic use, or a mixture of any two or more such protein and/or polypeptide. In one embodiment, the mixture may include one or more, natural or recombinant, protein or polypeptide for human or veterinary therapeutic use, or a mixture of any two or more such protein and/or polypeptide. In one embodiment, the mixture may include one or more protein or polypeptide derived from one or more, natural or recombinant, animal or human blood plasma or mixture of any two or more such protein and/or polypeptide. In one embodiment, the mixture may include one or more protein or polypeptide derived from one or more, natural or recombinant, plant material, or mixture of any two or more such protein and/or polypeptide. In one embodiment, the mixture may include one or more protein or polypeptide derived from one or more of animal or human milk or milk derived from a recombinant animal, or mixture of any two or more such protein and/or polypeptide. In one embodiment, the mixture may include one or more protein or polypeptide derived from one or more, natural or recombinant, avian egg, or mixture of any two or more such protein and/or polypeptide. In one embodiment, the mixture may include one or more protein or polypeptide derived from one or more, natural or recombinant, bacterium, yeast, fungus, virus or insect, or mixture of any two or more such protein and/or polypeptide. In one embodiment, the mixture may include one or more protein or polypeptide derived from one or more, natural or recombinant, mammalian cell culture or animal tissue, or mixture of any two or more such protein and/or polypeptide. In one embodiment, the mixture may include one or more organic compound, drug or drug intermediate, or mixture of any two or more thereof. In one embodiment, one or more of the one or more organic compound, drug or drug intermediate is chiral. In one embodiment, the mixture may comprise a mixture or combination of any of the foregoing, such as a mixture of an antibody and an enzyme, or a mixture of proteins and/or polypeptides obtained from plant material and an avian egg, or any mixture of any of the foregoing exemplary components to which the process of the present invention may be applicable.

In one embodiment, the process of the present invention further includes a step of detecting the displacer compound as it emerges from the stationary phase, wherein the detecting is by one or more of UV/Visible absorption spectroscopy, fluorescence emission spectroscopy, mass spectrometry, pH, conductivity and one or more electrochemical method. The foregoing are the most common applicable methods for detecting the displacer compounds; other suitable methods may be used as known in the art. Such detection may be of one or more "Y" substituents as discussed above.

In one embodiment, the method used to detect the component(s) being displaced from the stationary phase can be suitably determined based on the specific component sought. Thus, for example, proteins and polypeptides may be determined based on their UV/visible absorption spectra or wavelengths of characteristic absorption, or by derivatizing them with a visualizing agent. Similarly, drugs and drug intermediates may be determined based on their UV/visible absorption spectra or wavelengths of characteristic absorption.

In one embodiment, the process of the present invention further includes one or more steps of regenerating the stationary phase. In one embodiment, the regenerating may include, for example, treating the stationary phase with a solution of one or more of an alkali metal hydroxide, an alkali metal salt, an alkaline earth hydroxide, an alkaline earth salt, an organic acid, an alkyl sulfonic acid, a quaternary ammonium hydroxide, a quaternary ammonium salt, an alkyl amine, wherein the solution may further comprise a suitable pH buffer. Other suitable regenerating steps may be added, including simple washing with purified water, as needed and as appropriate. In one embodiment, the regeneration includes the use of an organic co-solvent together with water.

Figure 2:
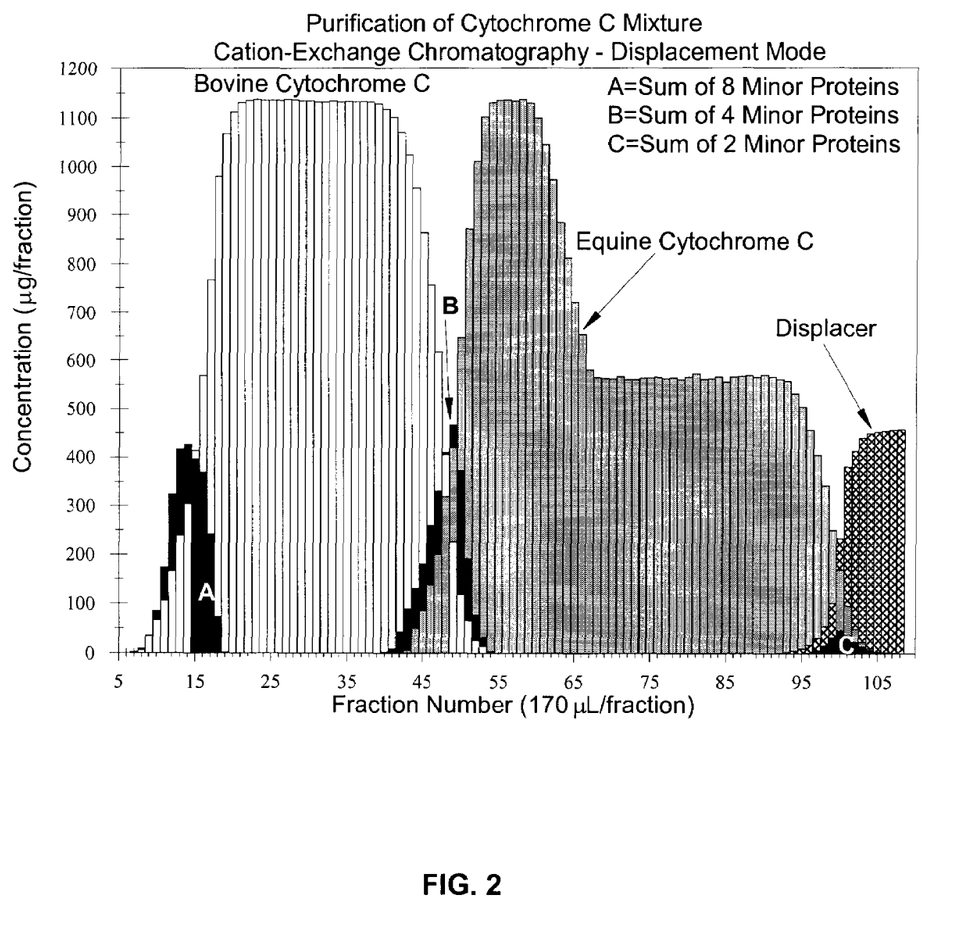
FIG. 2 is a graph depicting the concentration of fractions collected during displacement chromatography of a mixture of bovine cytochrome C and equine cytochrome C, in accordance with an embodiment of the invention.

In one embodiment, the present invention provides a process for one or more of detection, collection or quantification of trace components in the sample subjected to displacement chromatography. Although the process of the present invention may generally be used as a preparative purification method as described in the previous embodiments, displacement chromatography is also a powerful sample preparation technique which enables facile detection, collection and quantification of trace components in the sample. Sample components whose concentration is insufficient to saturate the capacity of the chromatographic resin at any point may not participate in the displacement train but may be instead carried along in the narrow transition zones between the major components in the sample and between the last major component and the displacer. This is clearly shown in FIG. 2 with the transition zones labeled A, B and C. Although not to be bound by theory, it appears that these trace components may not fully participate in the displacement chromatography process. In any case, the trace components come off the column and so can be detected, collected and/or quantified.

Isolation of the fractions corresponding to these transition zones provides samples which are significantly enriched (10-400×) in the trace components and significantly depleted in major component(s). This combination allows much easier identification and quantification of the minor components and impurities compared to the original sample. The analysis of these enriched samples can be done by any appropriate method, including elution chromatography on the same resin as used for the displacement chromatography. Alternatively, if sufficient quantities of the trace components are collected, these components may be subjected to displacement chromatography. This embodiment is useful in final product analysis, biomarker discovery, process control and process optimization. As used herein, the term "trace component" refers to relatively minor components present in the mixture subjected to displacement chromatography, and each such trace component may constitute from about 0.01 wt. % to about 10 wt. % of the mixture initially subjected to the displacement chromatography process of the present invention.

In the following examples, exemplary synthetic procedures are provided by which these exemplary cationic displacer compounds may be synthesized. Other suitable cationic displacer compounds within the scope of the invention can be synthesized by methods known to and/or adapted from the foregoing as will be understood by those of skill in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, in light of the present disclosure, those of skill in the art should appreciate that many changes can be made in the specific embodiments which are disclosed and still obtain a like or similar result without departing from the spirit and scope of the invention, which is limited only by the scope of the appended claims.

EXAMPLE 1

Synthesis of a Tetraquat, DBQ 1,3-Dichloro-2-propanol (DCP) is converted to 1,3-bis(N, N-dimethylamino)-2-propanol ("BDAP") by reaction with two equivalents of dimethylamine, essentially as described by Perrine (J. Organic Chemistry, vol. 18, pp. 1137-1141 (1953)). Then freshly distilled BDAP (146 g, 1 mole) and approx. 170 mL of water are charged to a round bottom flask fitted with a reflux condenser. An aqueous solution of N-(2-hydroxy-3-chloropropyl)-N-benzyl-N,N-dimethylammonium chloride (905 g @ 59.8% solids=541 g=2 moles) is added dropwise over a period of 3 hours. The resulting solution is stirred for 11 hours at room temperature. The solution is then heated to 50° C. and held at this temperature for 1 hour with continuous stirring, after which it is allowed to cool to room temperature. The resulting aqueous solution of DBQ is suitable for use as a displacer compound on a stationary phase such as a cation-exchange media. Solid DBQ, also suitable for use as a displacer compound, may be recovered by removal of water by rotary evaporation, followed by repeated precipitation from 2-propanol and final removal of solvent under high vacuum.

EXAMPLE 2

Synthesis of a Triquat, DMTQ

An aqueous solution of glycidyltrimethylammonium chloride (GMAC) (Aldrich, CAS #3033-77-0) found by titrimetric assay (tetrabutylammonium iodide/perchloric acid method) to contain 72.9 wt % active epoxy species is used. A solution of dimethylamine hydrochloride (408 g, 5 moles, Aldrich) in about 400 mL water is stirred vigorously in a round bottom flask fitted with a reflux condenser. To this is added 1040 g of the GMAC solution (=758 g active=5 moles) dropwise over about 1 hour with no external heating or cooling. This addition generally causes no noticeable exotherm. The resulting solution is stirred at room temperature for 1 hour after addition is complete. At this point dropwise addition of another equal portion of GMAC solution (5 moles) is started. This addition causes a strong exotherm, and continued addition of GMAC solution eventually will bring the solution to reflux. The rate of addition of this second GMAC charge is adjusted to keep the exotherm in control. When addition is complete the solution is stirred while it is allowed to cool. When its temperature reaches about 70° C. (after about 3 hours), external heating is applied with a heating mantle controlled by an electronic controller (J-Kem Electronics) at a setpoint of 70° C. The solution is kept at 70° C. for approx. 24 hours. Upon cooling to room temperature the solution of DMTQ is suitable for use as a displacer compound on a suitable stationary phase such as a cation-exchange media.

EXAMPLE 3

Synthesis of a Triquat, TBTQ-A

A stock solution of the triamine N-[3-(dimethylamino)propyl]-N,N',N'-trimethyl-1,3-propanediamine, also known as POLYCAT® 77, is prepared in 2-propanol and dried by stirring with $CaH_2$ for several days under dry $N_2$. To a 250 mL 3-neck round bottom flask fitted with a Teflon-coated thermocouple and a rubber septum is charged 107 mL of this filtered solution, containing 12.5 g of POLYCAT® 77 (0.06 moles), and a magnetic stir bar. The flask is flushed with nitrogen and sealed under a positive pressure of nitrogen. Benzyl bromide (35 g, 0.2 moles, Aldrich) is added over approximately 3 hours to the stirred flask through a Teflon needle at a constant rate by syringe pump. A mild exotherm is noted, raising the internal temperature to about 30° C. When addition of benzyl bromide is complete, the solution is heated at 40-45° C. for 14 hours, cooled to room temperature, evaporated to a viscous oil on a rotary evaporator, taken up in methanol and extracted with three 60 mL portions of cyclohexane, decolorized with carbon, filtered and evaporated to dryness to yield TBTQ-A as an off-white solid. This material is suitable for use as a displacer compound on a suitable stationary phase such as a cation-exchange media.

EXAMPLE 4

Synthesis of a Diquat, BTA

DCP (80 g, 0.6 moles) and 40% aqueous trimethylamine (188 g @ 40 wt %=75 g=1.27 moles) are charged to a 500 mL round bottom flask fitted with a reflux condenser. This mixture is heated to 75° C. and held at this temperature with vigorous magnetic stirring for 48 hours. At the end of this time the clear, colorless solution is allowed to cool to room temperature. The yield of BTA is >98%. Upon cooling to room temperature the solution of BTA is suitable for use as a displacer compound on a suitable stationary phase such as a cation-exchange media.

EXAMPLE 5

Synthesis of a Diquat, DBD

Benzyl bromide (87 g, 0.5 moles, Aldrich), 100 mL acetonitrile (HPLC grade, Fisher), and a magnetic stir bar are charged to a 500 mL 3-neck round bottom flask fitted with a thermocouple, which is then sealed under $N_2$. Distilled BDAP (35 g, 0.24 moles) is weighed into a graduated cylinder, then charged to a 60 mL addition funnel and rinsed in with 20 mL of dry acetonitrile. Dropwise addition of the resulting BDAP solution is carried out over 80 min. A strong exotherm is noted immediately; continued addition raised the solution temperature slowly to about 45° C. Addition may be accelerated near the end to maintain the temperature at about 45° C. When addition of BDAP solution is complete, a heating mantle is put in place and solution heated at 55° C. for 3 hours, then at 70° C. for 15 hours. The solution is cooled to room temperature, transferred to a recovery flask and rotary evaporated to a viscous liquid. This liquid is taken up in acetone/water and stripped again on a rotary evaporator, giving 122.7 g (100% yield) of DBD as a tan solid that is essentially 100% pure by analytical HPLC. This material is suitable for use as a displacer compound on a suitable stationary phase such as a cation-exchange media.

EXAMPLE 6

Displacement Chromatography of a Protein Mixture

Materials and equipment. Bovine Cytochrome C (Sigma, #C3131, m.w. 12,327) and equine Cytochrome C (Sigma, #C7752, m.w. 12,384) are used as received. By HPLC analysis they are about 87% pure and about 86% pure, respectively, with the remainder being damaged cytochrome molecules or isoforms that absorb at 280 and 430 nm. All other chemicals are ACS reagent grade or better, and are used as received unless otherwise noted. Buffer solvent is HPLC grade distilled water. The loading/equilibration buffer contains 25 mM MOPSO (2-hydroxy-3-(N-morpholino)propanesulfonic acid), adjusted to pH=7.0 with NaOH. Displacer solutions are prepared by diluting a concentrated stock solution with loading buffer to the desired concentration. All buffer solutions are helium purged and filtered through a 0.2 µm filter before use. Displacement experiments are conducted using a Knauer HPLC system (model K-1001 pump, model K-2600 UV detector, 4-channel degasser, and solvent organizer). Fraction analyses are conducted using a Waters HPLC system (model 600 pump and controller, model 996 PAD, and model 717plus Autosampler with refrigerated sample tray).

Column preparation. The stationary phase, a cation-exchange resin, Tosoh SP-5PW, loaded on a 6.0×150 mm column, is cleaned and regenerated using Method C (below) and then stored as the sodium form in the loading/equilibration buffer. The output of the column is passed through a UV/V is flow-detector monitored at 264 nm, a conductivity flow-cell and a pH flow-cell. The column is equilibrated with loading buffer at a flow rate of 0.17 mL/min. Once all three signals (UV absorbance, conductivity, pH) form a stable, level baselines (about 25 min., 1 CV), the displacement experiment is immediately initiated. Excessive equilibration time is avoided so as not to convert the top of column from the sodium form to the hydrogen form.

Breakthrough experiments. Using 4 mM solutions of bovine Cytochrome C in the loading buffer and of equine Cytochrome C in the loading buffer, breakthrough experiments are conducted at various flow rates between 0.1-0.5 mL/min. From these experiments, it is found that satisfactory and reproducible data may be obtained at 0.17 mL/min. The column saturation capacity is found to be 148 mg (34.7 mg/mL matrix) for bovine Cytochrome C, and 150 mg (35.2 mg/mL matrix) for equine Cytochrome C.

Figure 1:
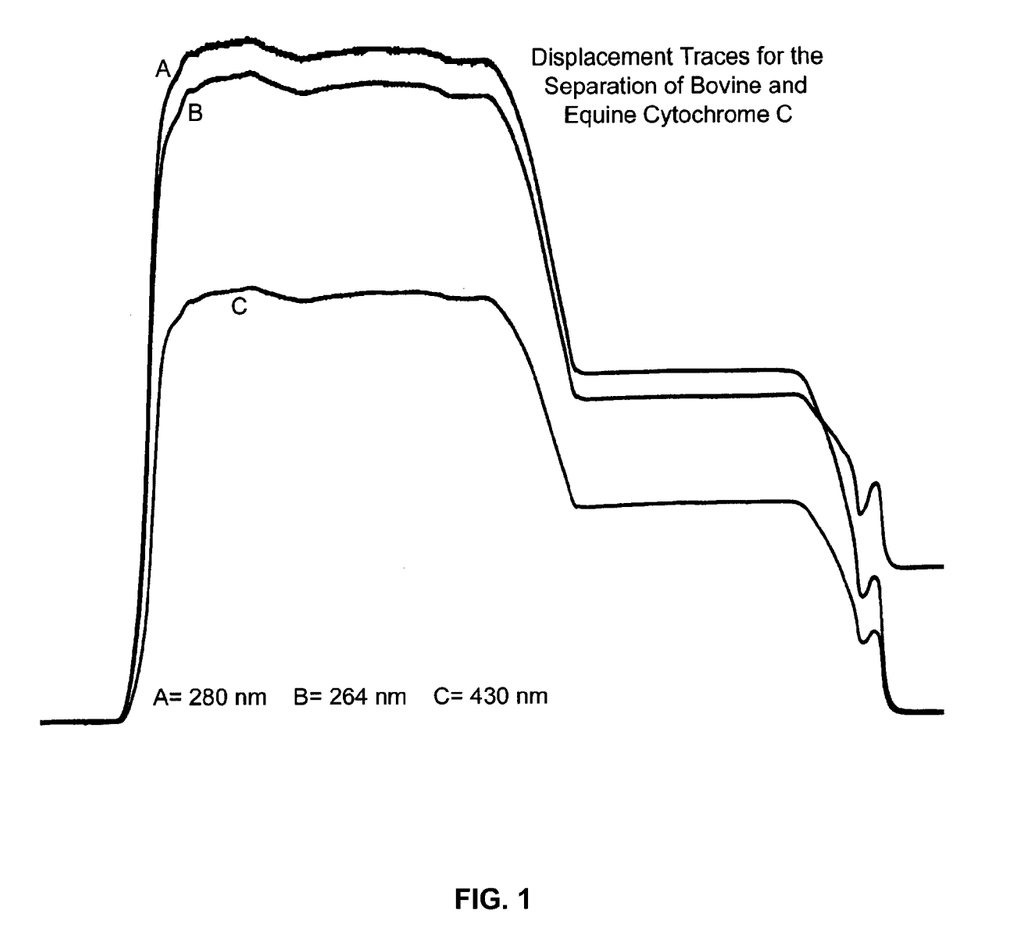
FIG. 1 is a graph depicting the output of a UV/V is HPLC detector at various wavelengths during displacement chromatography of a mixture of bovine cytochrome C and equine cytochrome C, in accordance with an embodiment of the invention.

Displacement experiment. Solutions of bovine Cytochrome C (4.12 mg/mL, Sigma #C3131, m.w.=12,327) and equine Cytochrome C (4.10 mg/mL, Sigma #C7752, m.w.=12,384) are prepared in the loading buffer. The protein concentrations are determined using BCA-Copper and Bradford assays. Equal volumes of the two cytochrome solutions are mixed, loaded into a 20.0 µL sample loop and then pumped onto the cleaned and properly equilibrated cation-exchange column at a constant flow rate of 0.17 mL/min. for 120 minutes. The loop is switched out of the input flow path, and the loading buffer is pumped through the column for 25 minutes at 0.17 mL/min. Finally, a 4.0 mM DBQ displacer solution in the loading buffer is pumped onto the column at 0.17 mL/min., and the output of the column is passed through a UV/V is flow-detector (10 µL flow-cell, monitored at 264, 280, 430 nm) into a fraction collector. The output of the UV/V is detector as a function of time is reproduced in FIG. 1.

No protein material is detected in the column effluent for approximately 70 minutes after displacer solution begins flowing into the column, so no fractions are collected during this time. Fraction 1 is collected at about 70 minutes after displacer flow begins, and subsequent fractions are collected at 1 minute intervals. Conductivity and pH flow-cells (see above) are usually in the output path behind the UV/V is detector in order to monitor the course of the displacement experiment; however, when fractions are collected, these two cells are switched out of the flow path so as not to broaden the transition between displacement peaks. A total of 108 fractions are collected. Once collected, the fractions are sealed and refrigerated for subsequent HPLC analysis. The displacement experiment is carried out at ambient temperature, 22° C.

HPLC analysis of displacement experiment fractions. All 108 fractions collected in the displacement experiment are subjected to HPLC analysis to determine the content of each. The conditions of this analysis are:
Column: Stainless steel, 4.6 (I.D.)×200 mm, PolySULFOET-HYL A, strong cation-exchange silica-based matrix, 5 μm particle size, 300 angstrom pore size, manufactured by PolyLC (Columbia, Md.)
Buffer Solvent: HPLC grade distilled water
Elution Buffers:
A-25 mM $NaH_2PO_4$, pH=6.8 with NaOH
B-500 mM NaCl+25 mM $NaH_2PO_4$, pH=6.8 with NaOH
Elution buffers were filtered through 0.2 μm filters to remove particulates.
Flow Rate: Constant at 1.0 mL/min.
Gradient method:
0-2 min 100% A, isocratic
2-62 min 100% A to 100% B, linear
62-72 min 100% B, isocratic
UV Detector:
264 nm-DBQ+total proteins,
280 nm-total proteins,
430 nm-cytochrome proteins only
Sample Prep: 30 μL of the fraction sample and 30 μL of freshly prepared 10 mM 1,4-dithiothreitol (DTT) are mixed. 50 μL of this mixture is injected onto the column.

The concentrations of components in each fraction are determined by integration of the analytical HPLC peaks. The results are compiled into the histogram displayed graphically in FIG. 2. Pure fractions are pooled to obtain the data compiled in Table 1. The recovery of total protein from the column is 98%.

TABLE 1

Results of Displacement Chromatography Using Displacer DBQ

| Purified protein: | Bovine Cytochrome C | Equine Cytochrome C |
|---|---|---|
| Sample pool: | 20-39 | 55-95 (early + late) |
| HPLC purity: | >99.9% | >99.9% |
| Recovery: | 63.4% | 78.3% |
| Measured DBQ:* | ND (<6 ppm) | ND(<6 ppm) |
| Estimated DBQ:* | <0.5 ppm | 2.5 ppm |

ND = not detected
*before dialysis

EXAMPLE 7

Displacement Chromatography of a Protein Mixture

Materials and equipment. Bovine Cytochrome C (Sigma, #C3131, approx. assay=89%) and bovine α-Chymotrypsinogen A (Sigma, #C4879, approx. assay=65%) are used as received. All other chemicals are ACS reagent grade or better, and are used as received unless otherwise noted. Buffer solvent is HPLC grade distilled water. The loading/equilibration buffer contains 25 mM MOPSO (2-hydroxy-3-(N-morpholino)propanesulfonic acid), adjusted to pH=7.0 with NaOH. Displacer solutions are prepared by diluting a concentrated stock solution with loading buffer to the desired concentration. All buffer solutions are helium purged and filtered through a 0.2 μm filter before use. Displacement experiments are conducted using a Knauer HPLC system (model K-1001 pump, model K-2600 UV detector, 4-channel degasser, and solvent organizer). Fraction analyses are conducted using a Waters HPLC system (model 600 pump and controller, model 996 PAD, and model 717plus Autosampler with refrigerated sample tray).

Column Preparation. The column (Amersham Mono S, 5.0×200 mm) is cleaned and regenerated using Method C (below) and then stored as the sodium form in a sodium chloride buffer, 2.0 M NaCl+25 mM MOPSO, pH=7.0 with NaOH. The output of the column is passed through a UV/V is flow-detector monitored at 264 nm, a conductivity flow-cell and a pH flow-cell. The column is equilibrated with loading buffer (see above) at a flow rate of 0.20 mL/min. Once all three signals (UV absorbance, conductivity, pH) form stable, level baselines (about 20 min., 1 CV), the displacement experiment is immediately initiated. Excessive equilibration time is avoided so as not to convert the top of column from the sodium form to the hydrogen form.

Breakthrough Experiments. Using 4.0 mg/mL solutions of bovine Cytochrome C in the loading buffer and of bovine α-Chymotrypsinogen A in the loading buffer, breakthrough experiments are conducted at various flow rates between 0.1-0.5 mL/min. The loading buffer is prepared from 25 mM MOPSO (2-hydroxy-3-(N-morpholino)propanesulfonic acid) and adjusted to pH=7.0 with NaOH. Good reproducible data are obtained at 0.20 mL/min. The column saturation capacity for Cytochrome C is about 198 mg (50.4 mg/mL matrix), and for Chymotrypsinogen is about 376 mg (95.7 mg/mL matrix). In these experiments, unpurified proteins are used straight out of the bottle.

Figure 3:
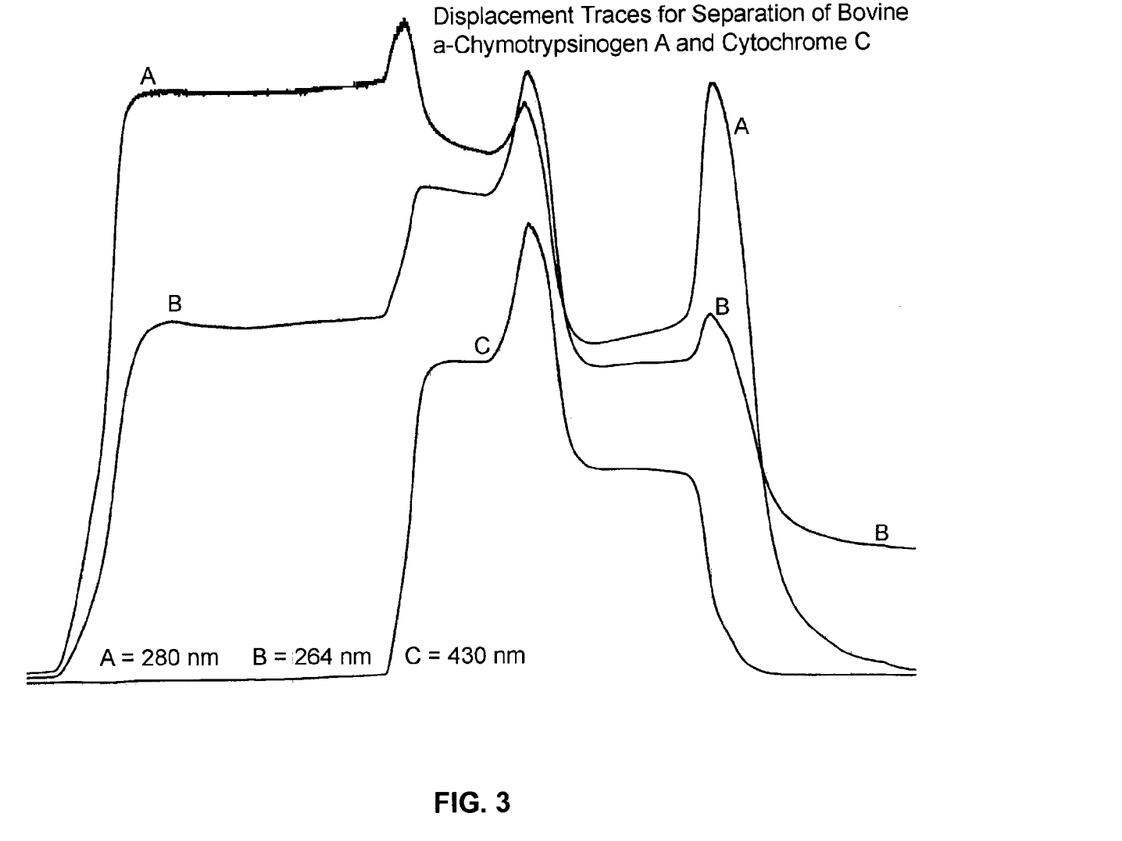
FIG. 3 is a graph depicting the output of a UV/V is HPLC detector at various wavelengths during displacement chromatography of a mixture of bovine cytochrome C and bovine α-chymotrypsinogen A C, in accordance with an embodiment of the invention.

Displacement Experiment. Solutions of bovine Cytochrome C (5.04 mg/mL, Sigma#C3131) and bovine α-Chymotrypsinogen A (9.96 mg/mL, Sigma#C4879) are prepared in the loading buffer (see above). The protein concentrations are determined using BCA-Copper and Bradford assays. Equal volumes of the two cytochrome solutions are mixed, loaded into a 20.0 mL sample loop and then pumped onto a cleaned and properly equilibrated the cation-exchange column (see above) at a constant flow rate of 0.40 mL/min. for 60 minutes. The loop is switched out of the input flow path, and the loading buffer is pumped through the column for 20 minutes at 0.20 mL/min. Finally, a 4.0 mM DBQ displacer solution in the loading buffer is pumped onto the column at 0.20 mL/min., and the output of the column is passed through a UV/V is flow-detector (10 μL flow-cell, monitored at 264, 280 nm) into a fraction collector. Fractions are collected every 1.00 min. Conductivity and pH flow-cells (see above) are usually in the output path behind the UV/V is detector in order to monitor the course of the displacement experiment; however, when fractions are collected, these two cells are switched out of the flow path so as not to broaden the transition between displacement peaks. Once collected, the fractions are sealed and refrigerated for subsequent HPLC analysis. The displacement experiment is carried out at ambient temperature, 22° C. The displacement trace is shown in FIG. 3.

HPLC Analysis of Proteins. The details of the HPLC fraction analysis is given below.
Column: Stainless Steel column 4.6×200 mm internal dimensions Manufactured by PolyLC (Columbia, Md.) PolySULFOETHYL A, strong cation-exchange silica-based matrix 5μ particle size, 300 angstrom pore size
Buffer Solvent: HPLC grade distilled water
Elution Buffers:
A-25 mM $NaH_2PO_4$, pH=6.8 with NaOH
B-0.50 M NaCl+25 mM $NaH_2PO_4$, pH=6.8 with NaOH
Elution buffers are filtered through 0.2 μfilter to remove particulates.

Flow Rate: Constant flow rate was 1.0 mL/min.
Gradient 0-2 min 100% A, isocratic
Method:
2-62 min 100% A to 100% B, linear gradient
62-72 min 100% B, isocratic
UV Detector 264 nm-DBQ+proteins,
Wavelengths: 280 nm-proteins, 430 nm-cytochrome
Sample Prep: 50 µL of the sample mixture is injected onto column.

Figure 4:
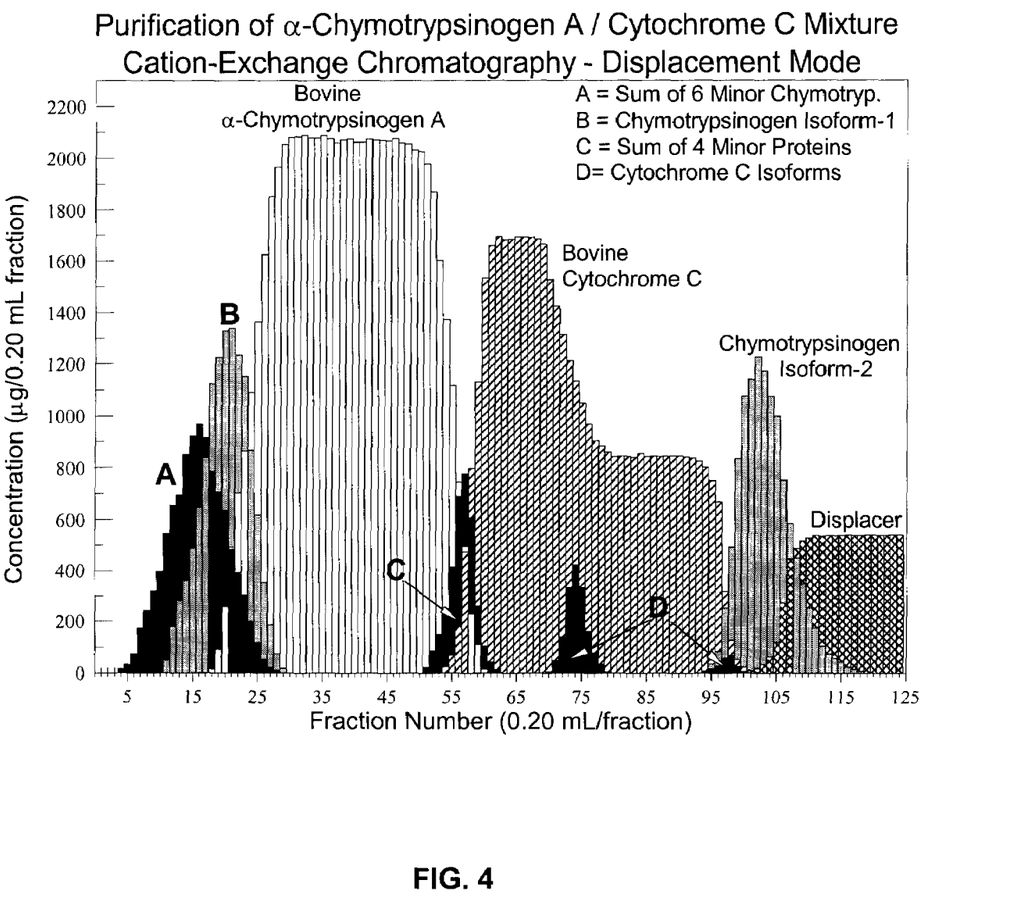
FIG. 4 is a graph depicting the concentration of fractions collected during displacement chromatography of a mixture of bovine cytochrome C and bovine α-chymotrypsinogen A C, in accordance with an embodiment of the invention.

All 125 collected samples are analyzed by the method described above, and the combined data from 264 nm, 280 nm and 430 nm are displayed in FIG. 4 and the table below. The recovery of protein from the column is nearly quantitative (>97%).

TABLE 2

| Purified protein: | bovine Chymo A | bovine Cyto C |
|---|---|---|
| Sample pool: | 30-50 | 63-69, 80-93 |
| HPLC purity: | >99.9% | >99.9% |
| Recovery: | 43.6 mg | 23.6 mg |
|  | 66% of major peak | 52% of major peak |
|  | 44% of total protein | 47% of total protein |
| Measured DBQ:* | ND (<6 ppm) | ND (<6 ppm) |
| Estimated DBQ:* | <0.5 ppm | <0.5 ppm |

ND = not detected
*before dialysis

Column Cleaning and Regeneration Procedures.

One or more of the following methods may be used to clean and/or regenerate the cation-exchange columns used in displacement procedures with displacer compounds such as DBQ. "Regeneration efficiency" is expressed as the percentage of the original column breakthrough capacity that is recovered after completion of the procedure. In each method, the steps are performed in the listed order and the flow rate is approximately 0.64 mL/min.

| Method A: Cleaning + Regeneration (regeneration efficiency 98%) | | |
|---|---|---|
| 2.0 M KCl + 0.1 M KOH | 180 min | 27 CV* |
| 0.1 M $KH_2PO_4$, pH = 6.5 w/KOH | 20 min | 3 CV |
| 15% glacial acetic acid | 27 min | 4 CV |
| 0.1 M $KH_2PO_4$, pH = 6.5 w/KOH | 20 min | 3 CV |
| 2.0 M NaCl + 25 mM MOPSO, pH = 7.0 | 34 min | 5 CV |

*CV = column volume

| Method B: Regeneration only (regeneration efficiency 95%) | | |
|---|---|---|
| 2.0 M KCl + 0.1 M $KH_2PO_4$, pH = 6.5 | 200 min | 30 CV* |
| 0.1 M $KH_2PO_4$, pH = 6.5 w/KOH | 20 min | 3 CV |
| 2.0 M NaCl + 25 mM MOPSO, pH = 7.0 | 34 min | 5 CV |

*Between 100 CV-150 CV (overnight regeneration) may be required to obtain 100% regeneration efficiency.

| Method C: Cleaning + Regeneration (regeneration efficiency 100%) | | |
|---|---|---|
| 2.0 M KCl + 0.1 M KOH | 80 min | 12 CV |
| 0.1 M $KH_2PO_4$, pH = 6.5 w/KOH | 20 min | 3 CV |
| 1.5 M $BaCl_2$ | 20 min | 3 CV |
| 0.1 M $KH_2PO_4$, pH = 6.5 w/KOH | 20 min | 3 CV |
| 15% acetic acid + 25 mM 18-crown-6 | 27 min | 4 CV |
| 0.1 M $KH_2PO_4$, pH = 6.5 w/KOH | 20 min | 3 CV |
| 2.0 M NaCl + 25 mM MOPSO, pH = 7.0 | 34 min | 5 CV |

| Method D: Cleaning + Regeneration (regeneration efficiency 100%) | | |
|---|---|---|
| 2.0 M KCl + 0.1 M KOH | 80 min | 12 CV |
| 0.1 M MOPS, pH = 7.2 w/NaOH | 20 min | 3 CV |
| 1.5 M $CaCl_2$ | 27 min | 4 CV |
| 0.1 M MOPS, pH = 7.2 w/NaOH | 20 min | 3 CV |
| 0.1 M $Na_2H_2EDTA$, pH = 8.0 w/NaOH | 20 min | 3 CV |
| 0.1 M MOPS, pH = 7.2 w/NaOH | 20 min | 3 CV |
| 15% glacial acetic acid | 27 min | 4 CV |
| 0.1 M MOPS, pH = 7.2 w/NaOH | 20 min | 3 CV |
| 2.0 M NaCl + 25 mM MOPSO, pH = 7.0 | 34 min | 5 CV |

| Method E: Regeneration only (regeneration efficiency 100%) | | |
|---|---|---|
| 2.1 M KCl | 80 min | 12 CV |
| 0.1 M MOPS, pH = 7.2 w/NaOH | 20 min | 3 CV |
| 1.5 M $CaCl_2$ | 27 min | 4 CV |
| 0.1 M MOPS, pH = 7.2 w/NaOH | 20 min | 3 CV |
| 0.1 M $Na_2H_2EDTA$, pH = 8.0 w/NaOH* | 20 min | 3 CV |
| 0.1 M MOPS, pH = 7.2 w/NaOH | 20 min | 3 CV |
| 2.0 M NaCl + 25 mM MOPSO, pH = 7.0 | 34 min | 5 CV |

*0.1 M $K_3$Citrate, pH = 7.0 may be used in this step.

| Method F: Cleaning + Regeneration (regeneration efficiency 100%) | | |
|---|---|---|
| 2.0 M KCl + 0.1 M KOH | 80 min | 12 CV |
| 0.1 M $KH_2PO_4$, pH = 6.5 w/KOH | 20 min | 3 CV |
| 2.0 M BDAP* + 50 mM acetic acid, pH = 4.6 w/HCl | 34 min | 4 CV |
| 1 M $KH_2PO_4$, pH = 6.5 w/KOH | 20 min | 3 CV |
| 2.0 M KCl + 0.1 M KOH | 20 min | 3 CV |
| 0.1 M $KH_2PO_4$, pH = 6.5 w/KOH | 20 min | 3 CV |
| 15% glacial acetic acid | 27 min | 4 CV |
| 0.1 M $KH_2PO_4$, pH = 6.5 w/KOH | 20 min | 3 CV |
| 2.0 M NaCl + 25 mM MOPSO, pH = 7.0 | 34 min | 5 CV |

*BDAP is 1,3-bis(dimethylamino)-2-hydroxypropane. In addition to BDAP, the following amines may be substituted as needed, based on cost and/or availability considerations: 1,3-diamino-2-hydroxypropane; 1,3-bis(dimethylamino)propane; bis(3-aminopropyl)amine; [bis(3-(dimethylamino)propyl)]aminomethane; 1-[bis(3-(dimethylamino)propyl)]amino-2-hydroxypropane; and 1,3-diaminopropane.

| Method G: Cleaning + Regeneration (regeneration efficiency 100%) | | |
|---|---|---|
| 2.0 M $[(Me_3NCH_2)_2CHOH]Cl_2$ + 0.1 M $[Me_4N]OH$ | 80 min | 12 CV |
| 0.1 M $KH_2PO_4$, pH = 6.5 w/KOH | 20 min | 3 CV |
| 1.5 M $BaCl_2$ | 20 min | 3 CV |
| 0.1 M $KH_2PO_4$, pH = 6.5 w/KOH | 20 min | 3 CV |
| 15% acetic acid + 25 mM 18-crown-6 | 27 min | 4 CV |
| 0.1 M $KH_2PO_4$, pH = 6.5 w/KOH | 20 min | 3 CV |
| 2.0 M NaCl + 25 mM MOPSO, pH = 7.0 | 34 min | 5 CV |

| Method H: Regeneration only (regeneration efficiency 99%) | | |
| --- | --- | --- |
| 2.0 M [(Me$_3$NCH$_2$)$_2$CHOH]Cl$_2$ + 0.1 M H$_3$PO$_4$, pH = 6.5 w/[Me$_4$N]OH | 160 min | 24 CV |
| 0.1 M KH$_2$PO$_4$, pH = 6.5 w/KOH | 20 min | 3 CV |
| 2.0 M NaCl + 25 mM MOPSO, pH = 7.0 | 34 min | 5 CV |

| Method I: Regeneration only (regeneration efficiency 99%) | | |
| --- | --- | --- |
| 2.0 M KBr + 0.1 M KH$_2$PO$_4$, pH = 6.5 w/KOH solvent = 80/20 v/v water/acetonitrile | 180 min | 27 CV |
| 0.1 M KH$_2$PO$_4$, pH = 6.5 w/KOH | 20 min | 3 CV |
| 2.0 M NaCl + 25 mM MOPSO, pH = 7.0 | 34 min | 5 CV |

All of the compositions and processes disclosed and claimed herein can be made and executed by those of ordinary skill in the art without undue experimentation in light of the present disclosure and based upon the knowledge of such persons. While the compositions and processes of this invention have been described in terms of certain preferred embodiments, it will be apparent to those of ordinary skill in the art that variations may be applied to the compositions and/or processes and in the steps or in the sequence of steps of the processes described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A displacement chromatography process, comprising:
   loading onto a suitable stationary phase a mixture comprising one or more component to be separated;
   displacing at least one of the one or more component from the stationary phase by applying to the stationary phase a mixture comprising a displacer compound having general formula (I):

wherein:
   each group $R_1$, $R_2$, $R_3$, $R'_1$, $R'_2$, and $R'_3$, independently may be selected from alkyl, aryl, and aralkyl, and in which a ring containing one or more quaternary nitrogen may be formed by any one or more of $R_1$ and $R_2$, $R_1$ and $R'_1$, $R_1$ and $R_4$, $R_4$ and $R'_4$, or $R_4$ and $R_5$;
   each $R_4$, $R'_4$, $R_5$ and $R'_5$ independently may be selected from alkyl, aryl, aralkyl and —(CH$_2$)$_a$—(CHY)$_b$—(CH$_2$)$_c$—N$^+$R$_1$R$_2$R$_3$ An$^-$, wherein $R_1$, $R_2$ and $R_3$ are as defined above;
   each Y independently may be selected from —H, —OH, —OR$_6$, halo, alkyl, aryl and aralkyl, wherein —R$_6$ may be alkyl or —(CH$_2$)$_a$—(CHOH)$_b$—(CH$_2$)$_c$—N$^+$R$_1$R$_2$R$_3$An$^-$, wherein $R_1$, $R_2$ and $R_3$ are as defined above, and one or more Y may be a group detectable by one or more electromagnetic methods;
   each q and z independently may be any whole number from 0 to about 6, with the proviso that q+z is equal to or less than about 6;
   each a, b, and c independently may be any whole number from 0 to 2, with the proviso that the sum a+b+c in any fragment is at least 1; and
   each An$^-$ independently may be one or more organic or inorganic, monovalent or polyvalent anion as needed to obtain a neutral compound.

2. The process of claim 1 wherein the stationary phase is a cation-exchange material.

3. The process of claim 1 wherein the one or more component comprises one or more polypeptide, one or more protein or a mixture of any two or more thereof.

4. The process of claim 3 wherein the one or more protein comprises a molecular weight of about 5 kD or higher.

5. The process of claim 3 wherein a protein and/or polypeptide from the mixture is displaced from the stationary phase in a fraction in which the protein and/or polypeptide is substantially enriched and/or in which the protein and/or polypeptide is substantially separated from other protein and/or polypeptide components.

6. The process of claim 5 wherein a protein and/or polypeptide from the mixture is displaced from the stationary phase in a fraction in which the protein and/or polypeptide is substantially enriched and/or in which the protein and/or polypeptide is substantially separated from other protein and/or polypeptide components.

7. The process of claim 3 wherein the mixture comprises two or more proteins, two or more polypeptides or a mixture thereof.

8. The process of claim 3 wherein the one or more polypeptide. one or more protein or mixture of any two or more thereof comprises one or more, natural or recombinant, antibody or a mixture of any two or more such antibodies.

9. The process of claim 3 wherein the one or more polypeptide, one or more protein or mixture of any two or more thereof comprises one or more, natural or recombinant, enzyme or a mixture of any two or more such enzymes.

10. The process of claim 3 wherein the one or more polypeptide, one or more protein or mixture of any two or more thereof comprises one or more, natural or recombinant, protein and/or polypeptide for diagnostic use, or a mixture of any two or more such protein and/or polypeptide.

11. The process of claim 3 wherein the one or more polypeptide, one or more protein or mixture of any two or more thereof comprises one or more, natural or recombinant, protein and/or polypeptide for human or veterinary therapeutic use, or a mixture of any two or more such protein and/or polypeptide.

12. The process of claim 3 wherein the one or more polypeptide, one or more protein or mixture of any two or more thereof comprises one or more protein and/or polypeptide derived from one or more, natural or recombinant, animal or human blood plasma or a mixture of any two or more such protein and/or polypeptide.

13. The process of claim 3 wherein the one or more polypeptide, one or more protein or mixture of any two or more thereof comprises one or more protein and/or polypeptide derived from one or more, natural or recombinant, plant material, or a mixture of any two or more such protein and/or polypeptide.

14. The process of claim 3 wherein the one or more polypeptide, one or more protein or mixture of any two or more thereof comprises one or more protein and/or polypeptide derived from one or more of animal or human milk or milk derived from a recombinant animal, or a mixture of any two or more such protein and/or polypeptide.

15. The process of claim 3 wherein the one or more polypeptide, one or more protein or mixture of any two or more thereof comprises one or more protein and/or polypeptide derived from one or more, natural or recombinant, avian egg, or a mixture of any two or more such protein and/or polypeptide.

16. The process of claim 3 wherein the one or more polypeptide, one or more protein or mixture of any two or more thereof comprises one or more protein and/or polypeptide derived from one or more, natural or recombinant, bacterium, yeast, fungus, virus or insect, or a mixture of any two or more such protein and/or polypeptide.

17. The process of claim 3 wherein the one or more polypeptide, one or more protein or mixture of any two or more thereof comprises one or more protein and/or polypeptide derived from one or more, natural or recombinant, mammalian cell culture or animal tissue, or a mixture of any two or more such protein and/or polypeptide.

18. The process of claim 1 wherein the mixture comprises at least two components to be separated.

19. The process of claim 1 wherein the mixture comprises the at least one component and at least one impurity.

20. The process of claim 1 further comprising detecting the displacer compound as it emerges from the stationary phase, wherein the detecting is by one or more of UV/Visible absorption spectroscopy, fluorescence emission spectroscopy, mass spectrometry, pH, conductivity and one or more electrochemical method.

21. The process of claim 1 further comprising regenerating the stationary phase.

22. The process of claim 21 wherein the regenerating comprises treating the stationary phase with a solution of one or more of an alkali metal hydroxide, an alkali metal salt, an alkaline earth hydroxide, an alkaline earth salt, an organic acid, an alkyl sulfonic acid, a quaternary ammonium hydroxide, a quaternary ammonium salt, an alkyl amine, wherein the solution may further comprise a suitable pH buffer.

23. The process of claim 21 wherein the regenerating comprises treating the stationary phase with a solution comprising water and an organic co-solvent.

24. The process of claim 1 wherein the displacer compound is DBQ.

25. The process of claim 1 wherein the displacer compound is DMTQ.

26. The process of claim 1 wherein the displacer compound is DBTQ.

27. The process of claim 1 wherein the displacer compound is TBTQ-A.

28. The process of claim 1 wherein the displacer compound is BTA.

29. The process of claim 1 wherein the displacer compound is DBD.

30. The process of claim 1 wherein the mixture comprises one or more organic compound, drug or drug intermediate, or a mixture of any two or more thereof.

31. The process of claim 30 wherein one or more of the one or more organic compound, drug or drug intermediate is chiral.

32. The process of claim 1 wherein the mixture comprises one or more trace component, and the process further comprises one or more of detection, collection or quantification of the trace components in the mixture.

* * * * *